United States Patent [19]
Karetny et al.

[11] Patent Number: 5,858,409
[45] Date of Patent: Jan. 12, 1999

[54] HYDROLYZED CELLULOSE GRANULATIONS FOR PHARMACEUTICALS

[75] Inventors: Marc S. Karetny, Philadelphia, Pa.; David F. Erkoboni, Lawrenceville, N.J.; Ronald S. Vladyka, Jr., Somerset, N.J.; Howard J. Stamato, Bridgewater, N.J.

[73] Assignee: FMC Corporation, Philadelphia, Pa.

[21] Appl. No.: 785,228

[22] Filed: Apr. 17, 1996

[51] Int. Cl.$^6$ ...................................................... A61K 9/14
[52] U.S. Cl. ........................ 424/489; 424/475; 424/470; 424/494; 424/480
[58] Field of Search ...................................... 424/687, 489, 424/425, 451, 496, 494, 465, 470

[56] References Cited

U.S. PATENT DOCUMENTS

| | | |
|---|---|---|
| 2,978,446 | 4/1961 | Battista et al. . |
| 3,111,513 | 11/1963 | Battista et al. . |
| 3,146,168 | 8/1964 | Battista . |
| 4,427,778 | 1/1984 | Zabriskie ................................ 435/277 |
| 4,533,674 | 8/1985 | Schmidt et al. . |
| 4,600,579 | 7/1986 | Salpekar et al. . |
| 4,605,666 | 8/1986 | Schmidt et al. . |
| 4,710,519 | 12/1987 | Finnan et al. . |
| 4,744,987 | 5/1988 | Mehra et al. ............................ 424/687 |
| 4,792,452 | 12/1988 | Howard et al. ......................... 424/475 |
| 4,844,907 | 7/1989 | Elger et al. ............................. 424/465 |
| 4,904,477 | 2/1990 | Ho et al. . |
| 5,466,469 | 11/1995 | Kuhrts .................................... 424/451 |
| 5,607,695 | 3/1997 | Ek et al. ................................. 424/468 |

*Primary Examiner*—Thurman K. Page
*Assistant Examiner*—William E. Benston, Jr.
*Attorney, Agent, or Firm*—Robert L. Andersen; Anthony L. Cupoli

[57] ABSTRACT

The present invention provides a method for preparing a spray-dried compressible granular formulation for preparing pharmaceutical tablets in which hydrolyzed cellulose is used as a granulation aid, the resulting granulations, and pharmaceutical tablets compressed from such granules. In these formulations there is employed from 1 to 97% by weight pharmaceutical active, from about 3 to 99% by weight hydrolyzed cellulose, based on the dry weight of the granulation, and optionally conventional granulation and/or tableting additives such as surfactants, disintegrants and antiadherents/flow aids.

7 Claims, No Drawings

HYDROLYZED CELLULOSE GRANULATIONS FOR PHARMACEUTICALS

The present invention relates to a method for granulation of active pharmaceutical compounds, to granular formulations thereof, and to pharmaceutical tablets made from such granular formulations. More specifically the invention relates to spray-drying an aqueous slurry of hydrolyzed cellulose and one or more pharmaceutical actives to form granular formulations for use in the manufacture of pharmaceutical tablets. The methods and compositions of this invention are particularly useful for pharmaceutical actives which are not readily compressible into tablets following dry blending of excipients and pharmaceutical active, such as ibuprofen and acetaminophen.

Neither ibuprofen nor acetaminophen is readily compressible into satisfactory tablets from a dry mix of excipients heretofore used in the art. To accomplish compression of such difficult-to-process pharmaceuticals into acceptable tablets, several techniques have been used, with varying degrees of success. As indicated above it is conventional to dry blend the active with various tableting additives, including microcrystalline cellulose, and to then compress the resulting blend into tablets. The resulting tablets tend to be friable and difficult to process commercially due primarily to insufficient tablet hardness. In an effort to circumvent these problems, it has been necessary to resort to more complex granulation techniques such as spray drying. For example, U.S. Pat. No. 4,904,477 discloses spray drying ibuprofen from a slurry containing pregelatinized starch, a disintegrant and a wetting agent. Another example is U.S. Pat. No. 4,710,519, which discloses a process for spray drying a slurry of acetaminophen and a binder, in which the binder may be, among other things, microcrystalline cellulose or a mixture of microcrystalline cellulose and hydroxypropylmethylcellulose. Thus, prior art efforts have focused on the use of microcrystallne cellulose as a granulation aid. In addition, U.S. Pat. No. 4,744,987 discloses spray drying a slurry containing finely divided calcium carbonate and either microcrystalline cellulose or the Precursor wet cake from which microcrystalline cellulose is formed. The resulting product is employed as an excipient in vitamin or other pharmaceutical formulations using conventional dry blending techniques.

In accordance with the present invention, there is provided a method for granulating pharmaceutical actives which comprises spray-drying an aqueous slurry of hydrolyzed cellulose and a pharmaceutical active. The method produces a relatively porous, substantially spherical, free flowing granular formulation which may be readily compressed into pharmaceutical tablets having improved hardness, decreased friability, and excellent dissolution characteristics. In another aspect, the invention provides a granular composition comprising dry particles of pharmaceutical active and hydrolyzed cellulose in which the hydrolyzed cellulose is firmly bonded to and substantially envelops the particles of pharmaceutically active material. In yet another aspect, the invention provides pharmaceutical tablets manufactured by compression of the granular composition of this invention.

In the process aspect of this invention, an aqueous slurry of hydrolyzed cellulose is employed, which is in large measure responsible for the improved properties the granular formulations of this invention and for the improved tablets made therefrom. In this aspect, the invention thus provides a process for preparing a granular composition for preparation of tableted pharmaceutical dosage forms comprising the steps of (a) intimately mixing the pharmaceutical active particles with a smooth uniform aqueous slurry of hydrolyzed cellulose to form a smooth uniform aqueous slurry consisting essentially of hydrolyzed cellulose and pharmaceutical active; and (b) spray-drying the resulting slurry at a temperature below the charring temperature of the hydrolyzed cellulose and the melting point of the pharmaceutical active, as measured by the temperature of the exhaust from the spray dryer. The advantages and benefits of this invention are most readily achieved when the conditions for spray-drying are selected to produce spray-dried particles which are relatively porous and substantially spherical, in which 90 percent of the granules are larger than about 50 microns and smaller than about 500 microns and median granule size is in the range of about 150 to 300 microns. It is a further advantage of the present invention to include in the slurry additional granulation and tableting additives, such as binders, fillers, disintegrants, flow aids, antiadherents, and/or surfactants, so that the resulting granules can be directly compressed into tablets with addition of nothing more than a lubricant.

As used in this specification and claims, the term hydrolyzed cellulose means a cellulosic material prepared by acid hydrolysis of cellulose. Although there are different ways of effecting this hydrolysis, a typical method for preparing hydrolyzed cellulose comprises the treatment of original cellulosic material, for example a wood-derived pulp, with an inorganic acid such as 2.5N hydrochloric acid solution for 15 minutes at the boiling temperature. This treatment has the effect of reducing the degree of polymerization (DP) to a relatively constant level. A DP of 125 means that the chain of cellulose is composed of 125 anhydroglucose units. Higher DP values represent longer chain lengths of cellulose, and lower values represent shorter chain lengths. The hydrolyzed cellulose in the slurries utilized herein should have a minimum of 85% of the material with a DP of not less than 50 nor more than 550. More preferably, 90% of this material should have an actual DP within the range of 75 to 500. Even more preferably, 95% of the material should have a DP of 75 to 450. The level-off average DP, that is, the average DP of the total hydrolyzed cellulose sample which is consistently approached for a particular type of pulp, should be in the range of 125 to 374, preferably in the range of 200 to 300. The source of the pulp being hydrolyzed results in variations of the level-off DP. Hydrolyzed cellulose as used in this invention is a known composition more fully described as level-off DP in U.S. Pat. No. 2,978,446 and 3,111,513, the disclosures of which is incorporated herein by reference.

The hydrolysis step described above effectively destroys noncellulosic components of the starting material as well as the fibrous, amorphous structure of the cellulose, leaving the crystallite material that is described above. Heretofore, the usual practice has been to dry this material after it has been washed with water to remove the acid and all soluble residues from the hydrolysis. A common method of drying is spray drying, the method in general use for the preparation of microcrystalline cellulose. It has been found that spray drying the crystallites prior to granulation and incorporation into tablets results in making the cellulose particles more dense, difficult to compress into tablets, and producing tablets which are highly variable, tend to be friable, and lack sufficient hardness for convenient processing.

Unexpectedly, the use of the crystallites that have not been previously dried, namely hydrolyzed cellulose, results in improved compressibility of the granular composition when it is spray dried. It is the spray drying of slurries of hydrolyzed cellulose in combination with active pharmaceutical ingredients, and, optionally, a surfactant, a disintegrant, and a flow aid, that is the essence of the invention and provides the benefits described herein.

The process to prepare the granulations of this invention begins with a slurry of hydrolyzed cellulose in water. The term slurry as used herein is intended to mean an aqueous suspension of hydrolyzed cellulose particles which have not previously been dried through application of heat or other evaporative means. It is, however, intended to include a slurry of hydrolyzed cellulose from which a significant portion of the water has been removed by mechanical means such as filtration. The water content may be reduced from about 90% to 55–65% to produce a suitable dewatered starting material for use in the present invention. Reconstitution for use in this process is accomplished by the simple addition of water to the material, followed by thorough mixing. Preferably, the slurry used as a starting material in the process will contain 15% to about 25% by weight solids.

The active pharmaceutical agent is then added to this hydrolyzed cellulose slurry, and the resulting slurry is mixed thoroughly. The ratio of pharmaceutical active to cellulosic solids in the slurry is directly proportional to the ratio and levels of these components desired in the finished granular formulation and ultimately in the tableted pharmaceutical product. As indicated below this may vary over a wide range in that the finished granule may contain from about 1 to 97% of pharmaceutical active and from about 3 to 99% cellulosic solids, the balance, if any, being conventional granulation and tableting additives, such as binders, fillers, disintegrants, flow aids, antiadherents, and/or surfactants.

Finally, sufficient water is added, if necessary, to provide a slurry having the maximum amount of solids that will permit this slurry to be pumped to a spray dryer. Maximizing the solids content minimizes the energy required for granulation and also has a beneficial effect on particle size and size distribution of the resulting granules. It is also advantageous to homogenize the slurry to provide a smooth homogeneous suspension prior to delivering the slurry to the spray dryer.

In general the slurry may comprise about 10–75% by weight of total solids, including pharmaceutical actives and any additives. It will be understood by those skilled in spray-drying that the viscosity of the slurry is dependent on the percentage of solids in the slurry to be spray dried and that the viscosity may directly depend, at least in part, on the nature and amount (drug loading) of the pharmaceutical active. For example, ibuprofen, which is essentially insoluble in water, when combined with the hydrolyzed cellulose slurry, forms a viscous slurry and requires that the solids in the slurry, including the pharmaceutical active, not exceed about 35% by weight.

An advantageous range of solids for ibuprofen is about 15–35%, preferably about 20–35%, most preferably about 28–33%. Acetaminophen and pseudoephedrine hydrochloride, on the other hand, are respectively sparingly and freely soluble in water, allowing the slurry to contain up to about 55% by weight solids, counting both the acetaminophen and pseudoephedrine hydrochloride as solids. An advantageous range of solids for these actives is about 35–55%, preferably 40–50%, most preferably about 43–47%.

As will also be understood by those skilled in the art, the specific type of dryer employed is not critical to the success of this invention. Drying may be done, for example, with a disk dryer or a tower dryer. If a disk dryer is utilized, a large diameter dryer is preferred, since smaller spray dryers have a tendency to produce smaller denser granules which are useful, but are not preferred. A preferred type of dryer is a tower dryer, particularly one fitted with a high pressure nozzle which is adapted to produce the desirable particle size distribution and flow characteristics which characterize the granulations produced in accordance with this invention. With either type of dryer high productivity rates are readily obtained due the ability to operate the spray dryers in a continuous, rather than batch, manner. It will also be appreciated that the method of atomization in the dryer is important and may affect the size and character of the resulting granules, regardless of which type of dryer is utilized. In these regards, some experimentation may be required in order to optimize the process for a particular blend of hydrolyzed cellulose and pharmaceutical active.

In spray drying of the resulting slurry, an important aspect of the process is the control of temperature within the spray dryer. The outlet temperature of the dryer must be controlled carefully to avoid charring the hydrolyzed cellulose and/or melting the pharmaceutical active. An outlet temperature above about 120° C. will char the cellulose, making it a requirement that the outlet temperature not exceed this value. When drying low-melting actives, such as ibuprofen, the outlet temperature should be kept below the melting point of the active ingredient. In the case of ibuprofen, the maximum temperature should preferably be about 70° C., whereas acetaminophen will tolerate outlet temperatures up to about 90° C. The dryer outlet temperature must therefore be selected for each specific active pharmaceutical ingredient. Temperatures within the range of about 60° C. to about 105° C. are advantageous, and preferred temperatures are in the range of about 60° C. to about 95° C.

The spray-dried granular product will normally contain less than 10% by weight moisture after the spray-drying step. To obtain granular materials having the preferred 5% moisture or the most preferred moisture content of 2.5% or lower, it may be advantageous to place a fluid bed dryer in series with the spray dryer. Both vibratory and non-vibratory fluid bed dryers are equally appropriate for this final drying step, which does not alter the structure and size of the granular particles, but merely removes additional water from them.

In accordance with the second aspect of this invention, the resulting granular composition comprises (a) from about 1 percent to about 97 percent (preferably 5 to 95%) by weight of particles of a pharmaceutical active and (b) from about 3 percent to 99 percent (preferably 5 to 90%) by weight of hydrolyzed cellulose intimately bonded to and substantially enveloping the pharmaceutical active particles. Advantageously, the composition is one in which about 90 percent of the granules are larger than about 50 microns and smaller than about 500 microns, and median granule size is in the range of about 150 to 300 microns.

The spray-dried granular compositions of the invention and the process to make them is applicable to virtually all pharmaceutical active agents, including combinations of these, regardless of whether the active agents are water-soluble or water-insoluble. Typical of such pharmaceutical active agents are: analgesics such as acetaminophen, ibuprofen, ketoprofen, indomethacin, naproxen, acetaminophen with codeine and acetaminophen with propoxyphene napsylate; antibiotics such as erythromycin, cephalosporins, and minocycline hydrochloride; antiepileptics such as phensuximide, phenytoin sodium, and valproate sodium; antihistamines such as chlorpheniramine maleate, diphenhydramine hydrochloride, and triprolidine hydrochloride; cough and cold drugs such as dextromethorphan hydrobromide, ephedrine sulfate, guiafenesin, phenylpropanolamine hydrochloride, promethazine hydrochloride, and pseudoephedrine hydrochloride; cardiovascular drugs such as captopril, chlorthiazide, hydrochlorthiazide, diltiazem, nadolol, papaverine hydrochloride, procainamide hydrochloride, propranolol hydrochloride, quinidine gluconate, quinidine sulfate, and nifedipine; gastrointestinal drugs such as cimetidine, loperamide hydrochloride, ranitidine, and famotadine; and respiratory drugs such as albuterol sulfate, aminophylline, and theophylline.

In order to produce granulations which are directly compressible into tablets, the granular compositions of the invention, and the slurry from which they are formed, may also advantageously be formulated to contain minor amounts of conventional granulation and/or tableting additives, such as surfactants, binders, fillers, disintegrants antiadherents and/or flow aids.

Suitable surfactants include sodium lauryl sulfate, dioctyl sodium sulfosuccinate, polyoxyethylene sorbitan fatty acid esters, such as TWEEN® polysorbates, and sorbitan fatty acid esters, such as SPAN® sorbitan esters. Sodium lauryl sulfate has advantageously been employed in the process of the invention. The surfactant may be present in about 0.01–1%, preferably 0.15–0.25%, most preferably about 0.15–0.22% by weight of the composition on a dry basis.

Suitable disintegrants include croscarmellose sodium, crospovidone, sodium starch glycolate, guar gum, magnesium aluminum silicate, copolymers of methacrylic acid with divinylbenzene, potassium alginate, starch, pregelatinized starch, or mixtures of two or more of the foregoing disintegrants. The amounts suitable for use in the invention varies widely within a range from about 0.1% to —5%, advantageously about 0.25% to about 3%, by weight of the composition on a dry basis. Preferred disintegrants are croscarmellose sodium, crospovidone, and sodium starch glycolate or combinations of these materials.

A flow aid or flow aid with antiadherent properties, such as colloidal silica, may also be incorporated In the method and granular composition, suitably at a level in the range of from about 0.1–3%, advantageously from 0.5–1%, preferably from 0.7–0.8%.

Such conventional additives may simply be added to the slurry from which the granular formulations of this invention are derived. However, those skilled in the art will appreciate that the order of addition and the level at which each of these additives is most beneficially employed in a particular formulation may require optimization within the variables set forth above. For example, for granulations of water insoluble or slightly soluble additives it is usually beneficial to add a surfactant prior to addition of the active material.

Formulations of ibuprofen and combinations of acetaminophen and pseudoephedrine hydrochloride serve as representative active agents which present difficult formulation problems that are quite different from each other. It is these extremes that indicate the breadth of applicability of the techniques describe herein to a wide variety of active agents. In the paragraphs which follow, all percentages are by weight of the solid components of the composition.

For ibuprofen compressible granular formulations of this invention, the ibuprofen content may range from about 40–90%, preferably from 60–70%, and most preferably from 63–67%, depending on the weight of the tablet being produced. The combinations of acetaminophen with pseudoephedrine hydrochloride may contain 40–90%, preferably 60–90%, and most preferably 75–85% of the former and 2–10%, more preferably 3–8%, and most preferably 4–5% of the latter active agent. Because of these differences in content of active pharmaceutical ingredient, the content of hydrolyzed cellulose varies inversely with the content of the active ingredient. For ibuprofen, the hydrolyzed cellulose may be present in 20–45%, more preferably 30–36%, most preferably 30–33%. On the other hand, for tablets comprising the combination of acetaminophen and pseudoephedrine hydrochloride, the hydrolyzed cellulose content is about 5–50%, more preferably 10–40%, and most preferably 11–13%. For other active pharmaceutical ingredients the range of hydrolyzed cellulose will be about 3–99% of the solids. The percentage of the other pharmaceutical actives may range from about 1–97%, depending on the properties of the specific material, and the dosage of the active agent that is to be delivered, and whether or not other additives are employed in the formulation.

The tableted compositions of this invention comprise the foregoing granular compositions and from about 0.5% to about 3% by weight of a compatible pharmaceutically acceptable lubricant, advantageously about 0.75–2%, preferably about 1–1.5% by weight of the tablets. The lubricants minimize wear and tear on the tableting machines and minimize adherence of the material to tooling surfaces. Suitable lubricants which may be used are stearic acid, magnesium stearate, calcium stearate, hydrogenated vegetable oils, talc, sodium stearyl fumarate and combinations thereof.

The following examples are presented for illustration purposes and not to limit the scope of the invention. The examples illustrate the best mode for practicing the invention including properties of the granular compositions, the methods by which these compositions are made, the incorporation into the granular compositions of granulation and tableting additives such as surfactants, disintegrants and antiadherents/flow aids, and the use of a tower spray dryer. Two very different active pharmaceutical ingredients are exemplified to illustrate the diverse materials which can be successfully formulated into spray-dried compressible granulations of this invention. It is believed that this method is advantageous for many other active ingredients, even though they may be able to be compressed directly from dry powder mixes or other known techniques. The advantages which make this desirable for easily compressed pharmaceutical actives are the high productivity of the spray-drying process and the resulting high productivity of tablets possessing an unusually high degree of uniformity in properties, as is demonstrated in Examples 1–3 below for ibuprofen and combinations of acetaminophen and pseudoephedrine hydrochloride. This method offers the additional potential of less severe tableting conditions which, in turn, reduce the wear on tableting machines, tools, and dies.

For comparison purposes, Example 4 corresponds directly with Example 2, except that Example 4 is prepared from an alternative source of cellulose, namely, microcrystalline cellulose. This material is to be distinguished from the hydrolyzed cellulose of this invention by the fact that it has already been spray dried and is reconstituted into the slurry. The use of this previously spray dried material results in a granular formulation which is not as compressible as the hydrolyzed cellulose granulation of the invention. This can readily be seen from the uniformly reduced hardness of tablets prepared at equivalent compression forces in Examples 2 and 4.

In the examples all percentages are by weight unless it is indicated to be otherwise. In these examples, the materials utilized, unless otherwise identified are as follows: colloidal silica (Cab-O-Sil®, Cabot Corp., Cab-O-Sil Div., Tuscola, Ill.); croscarmellose sodium (Ac-Di-Sol®, FMC Corporation, Philadelphia, Pa.); ibuprofen (Albemarle Corp., Baton Rouge, La.); acetaminophen (Hoechst-Celanese, Bishop, Tex.); pseudoephedrine hydrochloride (Ganes Chemical, Carlstadt, N.J.); tower dryer made by NIRO, Inc., Colombia, Md.;

EXAMPLE 1

In a 208 liter vat stirred with a Lightnin'® mixer was placed 58.400 kilograms of an aqueous slurry of hydrolyzed cellulose (21% solids). A solution of 0.064 kilograms of sodium lauryl sulfate in deionized water was prepared and added to the slurry. In sequence, 0.31 kilograms of colloidal silica, 1.100 kilograms of croscarmellose and 26.264 kilograms of ibuprofen were added to the vat. Sufficient deionized water was added to the vat to bring the total amount of water added to 47.20 kilograms. This reduced the solids in the slurry to 27.09%. After mixing the slurry for a short period of time, the mixer was changed to a high shear mixer which was used until the slurry was smooth and uniform. The average viscosity of 4611 centipoise at 18° C. was measured using a Brookfield LVT viscometer. This slurry was spray dried using a 5.94 meter (19.5 foot) tall tower dryer having a 2.44 meter (8 foot) width. The dryer was fitted with a high pressure nozzle having a 2.0 mm insert in the nozzle. The slurry was fed to the dryer by a nine-stage Moyno pump at a pressure of 6550 kPa. The outlet temperature of the dryer was 69.5° C. In line with the outlet of the tower dryer was a vibratory fluid bed dryer which was installed to increase the dryness of the product. This dryer was operated at an average temperature of 68° C., resulting in a product having 2.28% moisture content. The spray drying of this slurry required 16 minutes. The particle size distribution as determined by a Microtrac® instrument showed that 90% of the particles had a size <482.19 microns; the median particle size being 274.21 microns; and 10% of the particles were <162.71 microns. The composition of the granules on a dry weight basis was 65.66% ibuprofen, 30.66% hydrolyzed cellulose, 0.16% sodium lauryl sulfate, 2.75% croscamellose sodium, and 0.77% colloidal silica.

A mixture of 990 grams of the dried granular material and 10 grams of lubricant, (Sterotex® K, a hydrogenated mixture of soybean and castor oils, Karlshamns Co., Div. of Abitec, Columbus, Ohio) was placed in a Patterson-Kelly "V" type blender and mixed for 10 minutes. Previously the Sterotex K had been passed through a #60 U.S. standard sieve. This 9.5 mm special concave tooling. The properties of 10 tablets as determined by an Erweka Multi-check Tester are shown in Table 1.

TABLE 1

Mean Tablet Properties

| Compression Force (Kg) | Tablet Weight (mg) | Relative Std. Deviation. (%) | Tablet Hardness (kP) | Relative Std. Deviation (%) |
|---|---|---|---|---|
| 206 | 308 | 0.5 | 9.4 | 3.2 |
| 418 | 309 | 0.4 | 16.7 | 2.1 |
| 630 | 310 | 0.6 | 11.4 | 10.2 |
| 823 | 311 | 0.5 | 9.6 | 10.3 |
| 1046 | 311 | 0.5 | 8.3 | 17.1 |
| 1251 | 311 | 0.6 | 9.1 | 11.3 |

EXAMPLE 2

In a 264.8 litter Ross Double Planetary mixer was placed 45.790 kilograms of an aqueous slurry of hydrolyzed cellulose (21% solids). Then, 0.160 kilograms of sodium lauryl sulfate was added directly to the slurry which was subsequently diluted with some deionized water. In sequence, 0.584 kilograms of colloidal silica, 0.560 kilograms of croscarmellose sodium, 65.168 kilograms of acetaminophen, and 3.192 kilograms of pseudoephedrine hydrochloride were added to the mixer. Additional deionized water was added to the mixer to bring the total amount of water added to 61.603 kilograms. The resulting slurry contained 43.72% solids. After all of the components were thoroughly mixed, the slurry was passed through a Ross Homogenizer one time before being placed in a holding tank. At 23° C. the viscosity was 1312 centipoise as measured by a Brookfield LVT viscometer. This slurry was pumped from the holding tank to a 5.94 meter (19.5) tall tower dryer having a 2.44 meter (8 foot) width. The dryer was fitted with a high pressure nozzle containing a 2.0 mm insert and operated at 4482 kPa pressure. This drying operation required 28 minutes and yielded 36.97 kilograms of dry, granular product. The moisture content of granular material was 0.54%. Its particle size distribution as measure by a Microtrac® instrument showed that 90% of the granules were <359.99 microns, the median particle size was 171.56 microns, and 10% of the particles were <18.67 microns. The composition of the granules on a dry basis was acetaminophen 81.46%, pseudoephedrine hydrochloride 4.89%, hydrolyzed cellulose 12.02%, sodium lauryl sulfate 0.2%, croscarmellose sodium 0.7%, and colloidal silica 0.73%.

In a Patterson-Kelly "V" type blender 990 grams of the granular product and 10 grams of stearic acid (J. T. Baker) were blended for 5 minutes prior to preparing tablets on a Stokes B2 tablet press using 12.7 mm standard round tooling. The properties of 10 tablets as determined by an Erweka Multi-check Tester are shown in Table 2.

TABLE 2

Mean Tablet Properties

| Compression Force (Kg) | Tablet Weight (mg) | Relative Std. Deviation (%) | Tablet Hardness (kP) | Relative Std. Deviation (%) |
|---|---|---|---|---|
| 600 | 615 | 0.4 | 7.3 | 3.2 |
| 783 | 613 | 0.3 | 8.6 | 2.8 |
| 1003 | 616 | 0.5 | 11.4 | 5.8 |
| 1172 | 612 | 0.4 | 10.0 | 8.2 |
| 1384 | 616 | 0.3 | 12.7 | 12.8 |
| 1613 | 617 | 0.3 | 12.7 | 21.9 |
| 1800 | 612 | 0.3 | 10.6 | 22.2 |
| 2009 | 613 | 0.3 | 9.2 | 11.5 |

EXAMPLE 3

In a 264.8 liter Ross Double Planetary mixer was placed 87.600 kilograms of an aqueous slurry of hydrolyzed cellulose (21% solids). Then, 0.096 kilograms of sodium lauryl sulfate was added directly to the slurry which was subsequently diluted with some deionized water. In sequence, 0.462 kilograms of colloidal silica, 1.65 kilograms of croscarmellose sodium, and 39.396 kilograms of ibuprofen were added to the mixer. Additional deionized water was added to the mixer to bring the total amount of water added to 70.796 kilograms. The resulting slurry contained 29.8% solids. After all of the components were thoroughly mixed, the slurry was passed through a Ross homogenizer one time before being placed in a holding tank. At 20° C. the viscosity was 2038 centipoise as measured by a Brookfield LVT viscometer. This slurry was pumped from the holding tank to a 5.94 meter (19.5 foot) tall tower dryer having a 2.44 meter (8 foot) width. The dryer was fitted with a high pressure nozzle and 2.0 mm insert in the nozzle operated at 3447 kPa pressure. This drying operation required approximately 4 hours. A vibrating fluid bed dryer was placed in series with the tower dryer. The moisture content of the granular material coming out of the fluid bed dryer was 3.80%. Its particle size distribution as measured by a Microtrac® instrument showed that 90% of the granules were <535.80 microns, the median particle size was 298.91 microns, and 10% of the particles were <149.38 microns. A more complete determination of the particle size distribution was made using a Sonic Sifter for 2 minutes at an amplitude of 3. The sample had been passed through a 30 mesh screen prior to this determination. The particle size distribution determined in this way was: 1.89% (30–50 mesh, 297–590 microns); 18.87% (50–60 mesh, 250–297 microns); 32.08% (60–80 mesh, 177–250 microns); 16.98% (80–100 mesh; 149–177 microns); 7.55% (100–120 mesh, 125–149 microns); 16.98% (120–170 mesh, 88–125 microns), and 5.66% (<170 mesh, 88 microns). The composition of the granules on a dry basis was the same as in Example 1.

In a Patterson-Kelly "V" type blender 990 grams of the granular product and 10 grams of Sterotex K (a hydrogenated mixture of soybean and castor oils, sold by Karlshamns Co., Div. of Abitec, Columbus, Ohio) were blended for 5 minutes prior to preparing tablets on a Stokes B2 tablet press using 9.5 mm special concave round tooling. The properties of 10 tablets as determined by an Erweka Multi-check Tester are shown in Table 3.

TABLE 3

Mean Tablet Properties

| Compression Force (Kg) | Tablet Weight (mg) | Relative Std. Deviation (%) | Tablet Hardness (kP) | Relative Std. Deviation (%) |
| --- | --- | --- | --- | --- |
| 209 | 313 | 1.2 | 7.6 | 5.8 |
| 399 | 313 | 0.9 | 14.0 | 2.4 |
| 598 | 314 | 0.8 | 9.4 | 7.8 |
| 827 | 311 | 1.0 | 8.4 | 8.9 |
| 1017 | 312 | 0.9 | 8.0 | 11.8 |

EXAMPLE 4

In a 208.2 liter tank stirred with a Cowles' mixer were placed 28.848 kilograms of deionized water and 7.212 kilograms of microcrystalline cellulose (Avicel® PH-101, FMC Corporation, Philadelphia, Pa.). The microcrystalline cellulose was dispersed in the water, creating a smooth slurry. Then, 0.120 kilograms of sodium lauryl sulfate was added directly to the slurry which was subsequently diluted with some deionized water. In sequence, 0.438 kilograms of colloidal silica, 0.420 kilograms of croscarmellose sodium, 48.876 kilograms of acetaminophen, and 2.934 kilograms of pseudoephedrine hydrochloride were added to the tank. Additional deionized water was added to the tank to bring the total amount of water added to 44.485 kilograms. The resulting slurry contained 44.48% solids. After all of the components were thoroughly mixed, the slurry was placed in a holding tank. At 22° C. the viscosity was 1319 centipoise as measured by a Brookfield LVT viscometer. This slurry was pumped from the holding tank to a 5.94 meter (19.5 foot) tall tower dryer having a 2.44 meter (8 foot) width (made by Niro, Inc., Columbia, Md.). The dryer was fitted with a high pressure nozzle operated at 4826 kPa pressure. This drying operation required 15 minutes and yielded 28.12 kilograms of dry, granular product. The moisture content of this granular material was 1.21%. Its particle size distribution as measured by a Microtrac® instrument showed that 90% of the granules were <573.20 microns, the median particle size was 282.52 microns, and 10% of the particles were <156.37 microns. The composition of the granules on a dry basis was the same as in Example 2, except that the cellulose content resulted from use of microcrystalline cellulose rather than the hydrolyzed cellulose in of this invention.

In a Patteron-Kelly "V" type blender 990 grams of the granular product and 10 grams of stearic acid (J. T. Baker) were blended for 5 minutes prior to preparing tablets on a Stokes B2 tablet press using 12.7 mm standard round tooling. The properties of 10 tablets as determined by an Erweka Multi-check Tester are shown in Table 4.

TABLE 4

Mean Tablet Properties

| Compression Force (Kg) | Tablet Weight (mg) | Relative Std. Deviation (%) | Tablet Hardness (kP) | Relative Std. Deviation (%) |
| --- | --- | --- | --- | --- |
| 313 | 620 | 0.3 | 3.2 | 5.0 |
| 631 | 623 | 0.4 | 6.8 | 3.8 |
| 888 | 623 | 0.2 | 9.4 | 3.2 |
| 1163 | 615 | 0.2 | 8.5 | 33.8 |
| 1496 | 620 | 0.2 | 6.2 | 10.4 |
| 1806 | 610 | 0.7 | 7.1 | 14.4 |
| 2146 | 627 | 0.9 | 8.5 | 13.3 |

We claim:

1. A substantially porous spherical granular composition for compression into pharmaceutical tablets consisting essentially of 1 percent to 97 percent by weight of pharmaceutical active agent and 3 percent to 99 percent by weight of hydrolyzed cellulose.

2. The composition of claim 1 comprising spray dried particles consisting essentially of pharmaceutical active agent and hydrolyzed cellulose in which the hydrolyzed cellulose is bonded to the pharmaceutical active material to form a granular composition in which 90% of the granules are larger than 50 microns and smaller than 500 microns and median granule size in the range of 150 to 300 microns.

3. The composition of claim 1 or 2 in which the pharmaceutical active agent is selected from the group consisting of analgesics, antibiotics, cough and cold drugs, antiepileptics, antihistamines, cardiovascular drugs, gastrointestinal drugs, respiratory drugs, vitamins, and combinations of two or more of these classes of drugs.

4. The composition of claim 3 in which the pharmaceutical is selected from the group consisting of ibuprofen and acetaminophen and pseudoephedrine hydrochloride.

5. The composition of claim 1 or 2 additionally containing one or more compatible pharmaceutically acceptable additives selected from the group consisting of from 0.01 to 1 percent by weight of a surfactant, from 0.1 to 5 percent by weight of a disintegrant, and from 0.01 to 3 percent by weight of a flow aid.

6. Compressed pharmaceutical tablets comprising a compatible pharmaceutically acceptable lubricant and the composition of claim 1 or 2.

7. Compressed pharmaceutical tablets comprising a compatible pharmaceutically acceptable lubricant and the composition of claim 3.

* * * * *